(12) United States Patent
Schumacher

(10) Patent No.: US 11,481,903 B2
(45) Date of Patent: Oct. 25, 2022

(54) ITERATIVE BRANCHING STRUCTURE SEGMENTATION METHOD AND SYSTEM

(71) Applicant: MeVis Medical Solutions AG, Bremen (DE)

(72) Inventor: Mona Schumacher, Diepholz (DE)

(73) Assignee: MeVis Medical Solutions AG, Bremen (DE)

( * ) Notice: Subject to any disclaimer, the term of this patent is extended or adjusted under 35 U.S.C. 154(b) by 319 days.

(21) Appl. No.: 16/369,457

(22) Filed: Mar. 29, 2019

(65) Prior Publication Data

US 2020/0286238 A1 Sep. 10, 2020

(30) Foreign Application Priority Data

Mar. 8, 2019 (EP) ..................................... 19161750

(51) Int. Cl.
*G06K 9/00* (2022.01)
*G06T 7/11* (2017.01)
*G16H 30/40* (2018.01)
*G06N 3/04* (2006.01)

(52) U.S. Cl.
CPC .............. *G06T 7/11* (2017.01); *G06N 3/0454* (2013.01); *G16H 30/40* (2018.01); *G06T 2207/10081* (2013.01); *G06T 2207/20084* (2013.01); *G06T 2207/30056* (2013.01); *G06T 2207/30101* (2013.01)

(58) Field of Classification Search
None
See application file for complete search history.

(56) References Cited

U.S. PATENT DOCUMENTS

| 2003/0056799 | A1* | 3/2003 | Young | G06T 7/12 |
| | | | | 600/425 |
| 2016/0239956 | A1* | 8/2016 | Kang | A61B 6/032 |
| 2019/0205606 | A1* | 7/2019 | Zhou | G06N 3/0454 |
| 2021/0209766 | A1* | 7/2021 | Cho | G06N 3/08 |

FOREIGN PATENT DOCUMENTS

CN 103886312 A 6/2014

OTHER PUBLICATIONS

Gao, Xurong, et al. "Retinal blood vessel segmentation based on the Gaussian matched filter and U-net." 2017 10th International Congress on Image and Signal Processing, BioMedical Engineering and Informatics (CISP-BMEI). IEEE, 2017. (Year: 2017).*

(Continued)

*Primary Examiner* — Sean M Conner
(74) *Attorney, Agent, or Firm* — Laurence & Phillips IP Law

(57) ABSTRACT

Some embodiments include a method, comprising: receiving an image representing a branching structure; determining a starting feature of the branching structure; selecting a subregion of the image based on the starting feature; segmenting the branching structure in the subregion; generating a set of next features based on the segmented branching structure; and for each of the next features, repeating the selecting of the subregion based on the next feature, the segmenting of the branching structure, and the generating of the set of next features.

21 Claims, 16 Drawing Sheets

(56) References Cited

OTHER PUBLICATIONS

Ronneberger, Olaf; Fischer, Philipp; Brox, Thomas. U-net: Convolutional networks for biomedical image segmentation. In: International Conference on Medical image computing and computer-assisted intervention. Springer, Cham, 2015. S. 234-241.

Lessmann, Nikolas, et al. Iterative fully convolutional neural networks for automatic vertebra segmentation and identification, Preprint submitted to Medical Image Analysis, arXiv:1804.04383 (Nov. 26, 2018).

Lessmann, Nikolas, et al. Iterative fully convolutional neural networks for automatic vertebra segmentation. 1st Conference on Medical Imaging with Deep Learning (MIDL 2018), Amsterdam, The Netherlands.

Januszewski, Michal, et al. Flood-filling networks. arXiv preprint arXiv:1611.00421, 2016.

Bas, Erhan, et al., "Automated extraction of blood vessel networks from 30 microscopy image stacks via multi-scale principal curve tracing," 2011 8th IEEE Int'l Symposium on Biomedical Imaging: From Nano to Macro (ISBI 2011), IEEE, United States (Mar. 30, 2011).

Nadeem, Syed Ahmed, et al., "An Iterative Method for Airway Segmentation using Multiscale Leakage Detection," Progress in Biomedical Optics and Imaging, SPIE—International Society for Optical Engineering, Bellingham, WA, U.S., vol. 10133 (Feb. 24, 2017).

EP19161750, European Search Report (dated Apr. 15, 2019).

EP19161750, European Search Report (Form 1507) (dated Apr. 15, 2019).

\* cited by examiner

ITERATIVE BRANCHING STRUCTURE SEGMENTATION METHOD AND SYSTEM

RELATED APPLICATION

The present application claims priority to European Patent Application No. 19161750.5, filed on Mar. 8, 2019, titled "Iterative Branching Structure Segmentation Method and System," and assigned to the assignee of the present invention. European Patent Application No. 19161750.5 is incorporated by reference herein.

BACKGROUND

Branching structures occur frequently in a variety of systems. Examples of such systems include vascular systems in humans, animals, and plants. These branching structures may be segmented into a form better suited for a following procedure than an image. In a particular example, a vascular structure of a liver may be segmented to plan for an operation on the liver. The segmentation of the vasculature of a liver may be a time-consuming manual process. Automated processes may lack necessary detail.

DETAILED DESCRIPTION

Embodiments described herein relate to segmentation of branching structures and, in particular, systems and methods for segmenting branching structures represented by images.

In some embodiments, the operation of segmenting a branching structure may be divided. A branching structure may include a variety of structures. For example, the branching structure may include vascular systems, airways, or the like in humans, animals, and plants. Other examples include surface or underground formations that include branching pathways, materials, or the like. These branching structures have portions that split into two or more portions that may themselves split into two or more portions. Any branching structure that may be represented in an image may be a branching structure that may be segmented as described herein.

The segmentation may be divided into multiple parts in order to better capture the n-dimensional structure of the branching structure and to recognize large as well as small structures more accurately and efficiently. The segmentation may be an iterative process. As will be described in further detail below, iterating from a starting feature and operating on subregions may improve the segmentation performance. In particular, some segmentation processes such as automatic vascular segmentation within a liver may be a challenging task since structures from several millimeters to fractions of millimeters such as about 75 to about 300 μm, the length of a pixel, or less should be detected.

Figure 1:
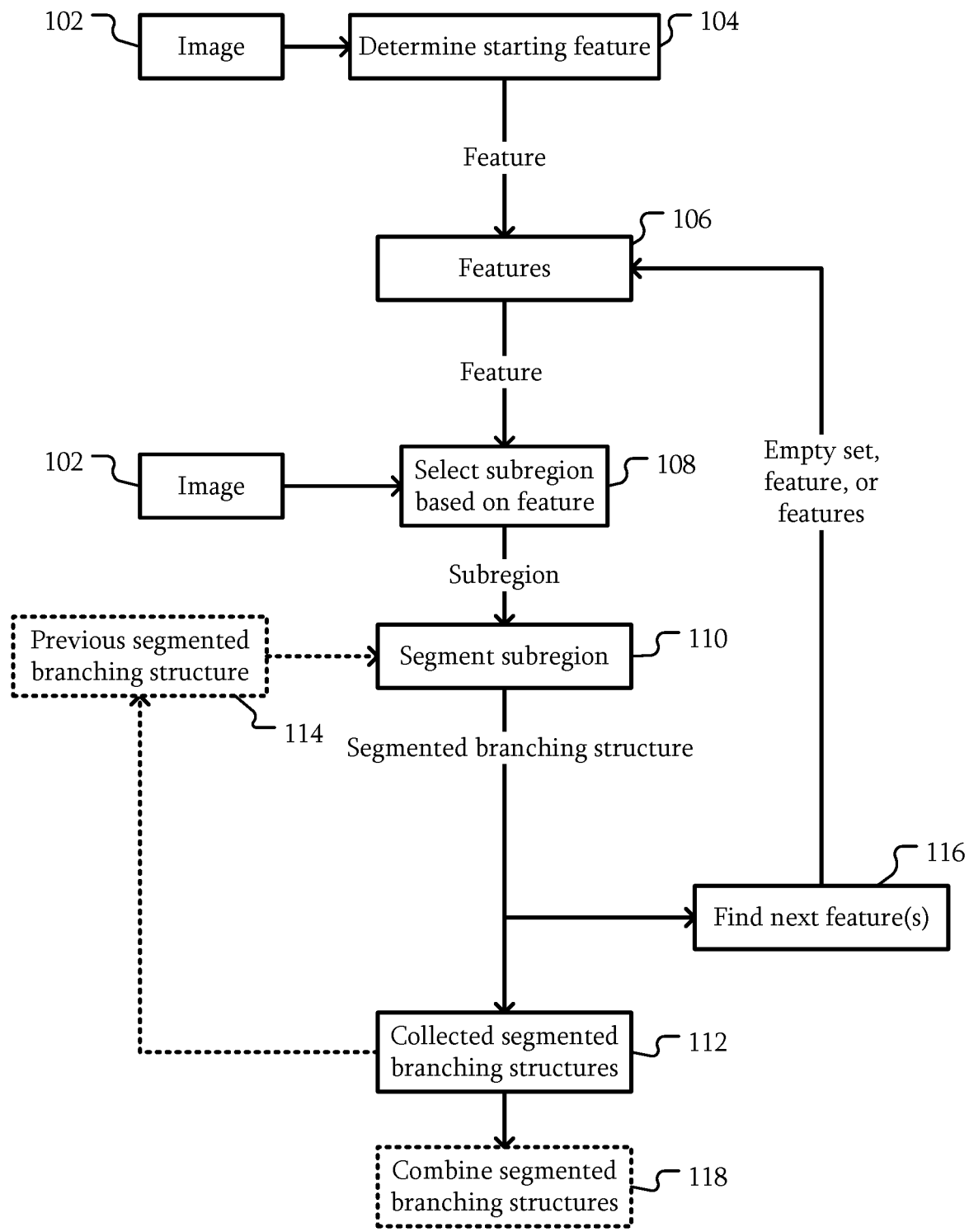
FIG. 1 is a block diagram of techniques of segmenting a branching structure according to some embodiments.

FIG. 1 is a block diagram of techniques of segmenting a branching structure according to some embodiments. An image 102 is data representing a branching structure. The image 102 may include a 2-dimensional (2-D or 2D), 3-dimensional (3-D or 3D), or n-dimensional representation of the branching structure. The image 102 may be received by a segmentation system. For example, the segmentation system may be integrated with a computed tomography system. The CT system may be configured to generate a 3-D CT image and process the image as described herein. In other embodiments, the segmentation system may receive the CT image from the CT system over a communication network. Although a CT image has been used as an example of the image 102, the image 102 may be generated by different imaging systems, such as magnetic resonance imaging (MRI), optical, ultrasonic, or other imaging systems.

In 104, a starting feature of the image 102 is determined. A feature may be a point, a line, a surface, a volume, an aggregation of associated pixels or voxels, or the like. In some embodiments, a user may view a representation of the image 102. Through a user interface, the user may select a feature. In other embodiments, an automated system, such as a neural network may be configured to analyze the image 102 to determine the starting feature. For example, the neural network may be configured to identify a largest portion of a branching structure within the image 102. In some embodiments, the starting feature may be determined by a model representing a larger structure encompassing the branching structure. In some embodiments, the starting feature may be a feature at the perimeter of the image 102.

The starting feature is the seed of the features 106. The features 106 is a collection of features that have been identified in the process of segmenting the branching structure represented by the image 102. The collection may be maintained in a variety of ways. For example, the collection may be maintained as a linked list, a stack, or other data structures. As will be described in further detail below, each feature of the features 106 may be used in the segmentation of the branching structure represented by the image 102.

A feature is selected from the features 106. As the starting feature is the only current feature, the starting feature is the selected feature. In 108, a subregion of the image 102 is selected based on the starting feature. The subregion is a region of the image 102 that is smaller than the whole. For example, if the image 102 is a 4096×4096×4096 voxel image, a subregion may be a 64×64×64 voxel region of the image 102. The subregion may be referred to as the region of interest (ROI). As will be described in further detail below, a subregion will be segmented. Thus, a subregion must be capable of being segmented. That is the subregion must be a large enough region of the image to contain a sufficient amount of information to allow that subregion to be divided into segments if it can be divided. However, any particular subregion need not be able to be segmented. For example, a subregion may be entirely within a single segment. Thus, that subregion would not be segmented while, if it had different information, it could have been segmented. In particular, a single pixel, voxel, or other similar unitary image element may not be divisible into segments while a collection of such unitary image elements would be divisible into segments. In some embodiments, a subregion has at least one dimension extending at least two image elements. For example, a subregion may have a size of 1×32 pixels, 32×1×1 voxels, or the like. In other examples, a subregion may have a size of 32×32×1 voxels. While one or more of the dimensions in image elements may be a single image element, at least one dimension extends for at least two image elements.

The subregion may be selected in a variety of ways. For example, the subregion may be a subregion centered on the feature. In a particular example, the feature may be a point on the image 102. The subregion may be centered on that point.

In 110, the branching structure in the subregion is segmented. For example, a neural network may use the subregion as an input. The neural network may be configured to analyze the subregion to segment the subregion. In a particular example, a U-net convolutional neural network (CNN) may be used to segment the subregion. The result is a segmented branching structure. A CNN is a class of deep neural networks (DNNs), commonly applied to analyzing visual imagery using deep learning. A DNN is an artificial neural network (ANN) with multiple layers between the input and output layers. CNNs use a variation of multilayer perceptrons designed to require minimal preprocessing compared to other image classification algorithms. The U-net is a CCN developed for biomedical image segmentation based on the fully convolutional network with an architecture modified and extended to work with fewer training images and to yield more precise segmentations.

The segmented branching structure may be collected in 112. In some embodiments, segmented branching structures may merely be stored for later use such as combining into a unified segmented branching structure in 118. In other embodiments, the segmented branching structure from the most recently processed subregion may be combined iteratively with other segmented branching structures from other subregions.

In 116, the segmented branching structure is used to generate a set of next features. The set of next features are features that indicate where the branching structure in the image continues beyond the subregion. For example, a neural network may use the segmented branching structure as an input. The neural network may be configured to analyze the segmented branching structure to determine the set of next features. For a given segmented branching structure, the set of features may be the empty set, a single feature, or multiple features. These features are added to the set of features in 106.

The sequence repeats for each of the features 106. As described above, the starting feature was the only initial feature. After the first iteration, additional features may be added to the features 106. Each of these features 106 may be used to select a subregion in 108. That subregion may be segmented in 110. The segmented branching structure is collected in 112 and used to generate the next features for 106. The process continues until each feature has been processed and no features remain in the features 106. As a result, beginning with the starting feature, new features are iteratively found and processed following the branching structure.

The resulting collected segmented branching structures are combined in 118 to form a segmented branching structure for the image 102. In some embodiments, the combined segmented branching structure is iteratively created with each recently segmented branching structure being added to the combined segmented branching structure. The segmented branching structures can be combined to form a binary image, a 2-D, 3-D, or other n-dimensional model, or the like.

In some embodiments, the segmenting of the subregion in 110 may be performed using a previously segmented branching structure 114. For example, after a segmented branching structure for a first subregion is generated in 110, features for that subregion may be found in 116. For one, some, or all of those features, a subsequent subregion may be selected in 108. When that subsequent subregion is segmented in 110, the segmented branching structure generated from that first subregion is used as the previous segmented branching structure 114. In some embodiments, the previous segmented branching structure 114 may be a second input to a neural network configured to segment the current subregion in 110. The use of the previous segmented branching structure 114 may improve the performance of segmenting the current subregion. In particular, as the first subregion and the current subregion may overlap, some of the branching structure segmented in the current subregion may match that of the previous segmented branching structure 114.

Accordingly, in some embodiments, segmentation operations include three categories of operations. In a first category, the root of the branching structure may be detected. This detected root is the starting feature of the iterative approach to segment the branching structure. The second category includes segmenting the subregion selected based on the current feature. The segmentation may be performed using a previously segmented branching structure including a segmented branching structure from a single subregion or a segmented branching structure aggregated from multiple subregions. The third category includes finding new features. These new features are the basis of subsequent selection of subregions and segmentation of those subregions. The process may repeat until no new features are detected.

Figure 2A:
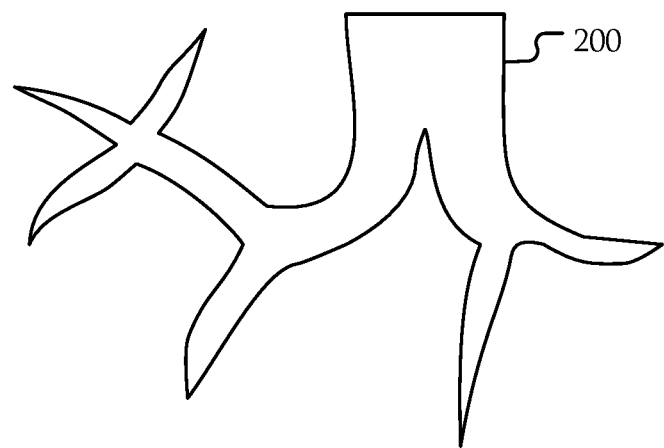
FIGS. 2A-2V are diagrams of an example of segmenting a branching structure in an image according to some embodiments.
Figure 2B:
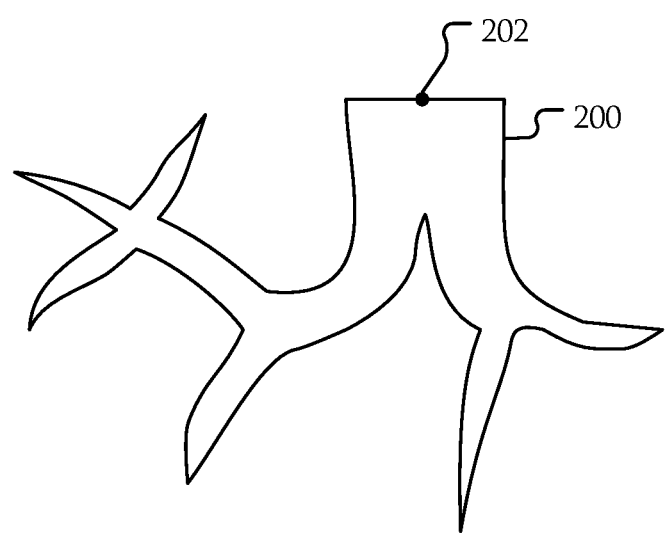
Figure 2C:
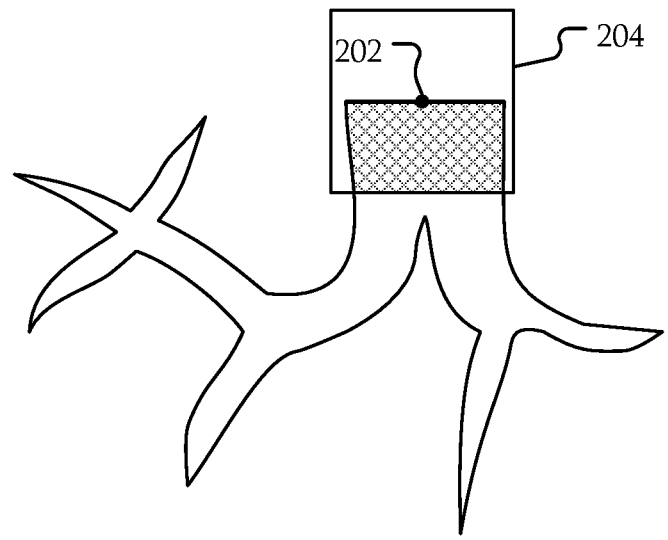
Figure 2D:
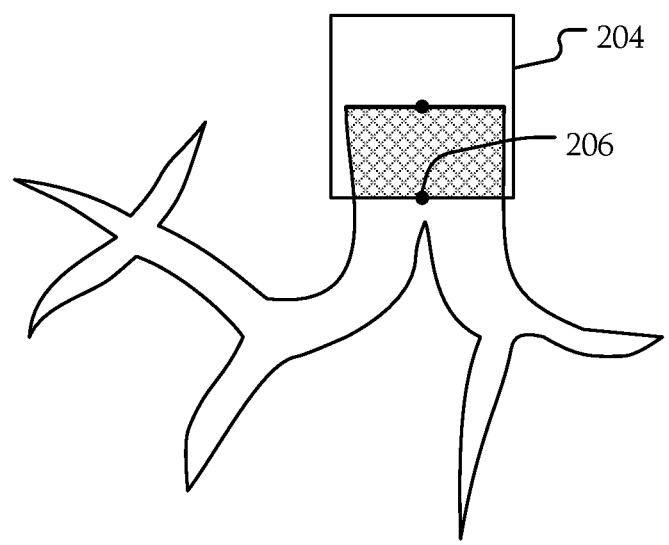
Figure 2E:
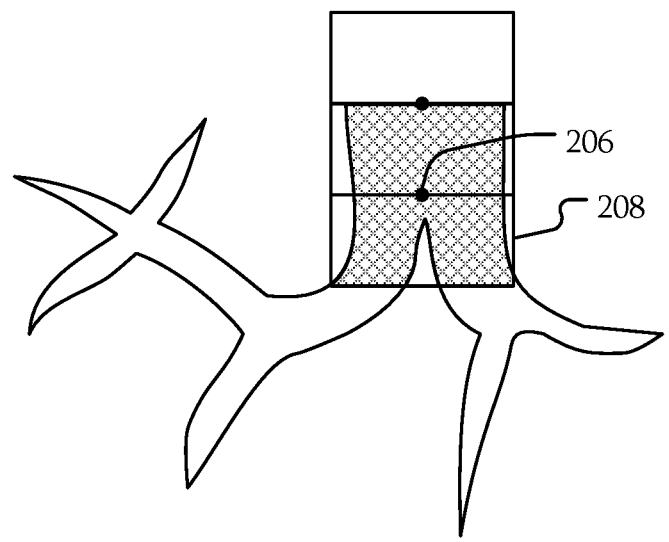
Figure 2F:
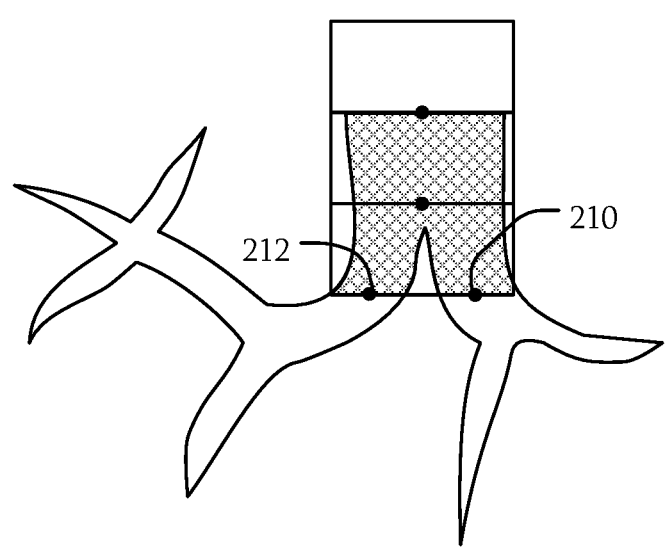
Figure 2G:
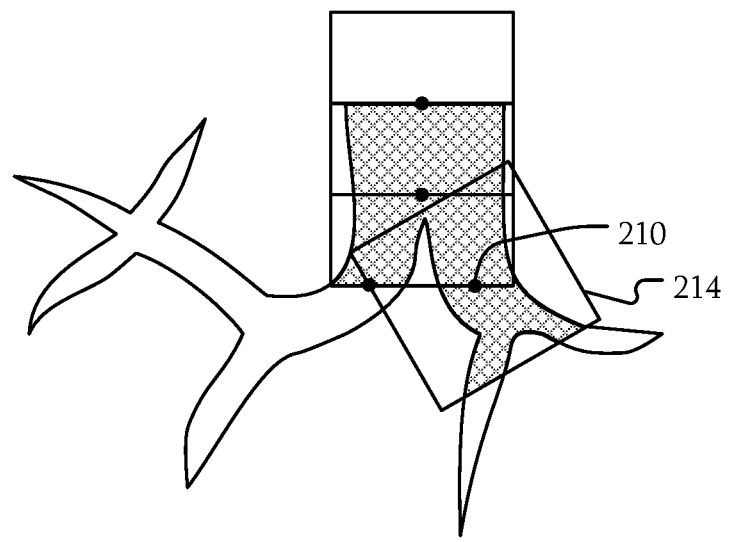
Figure 2H:
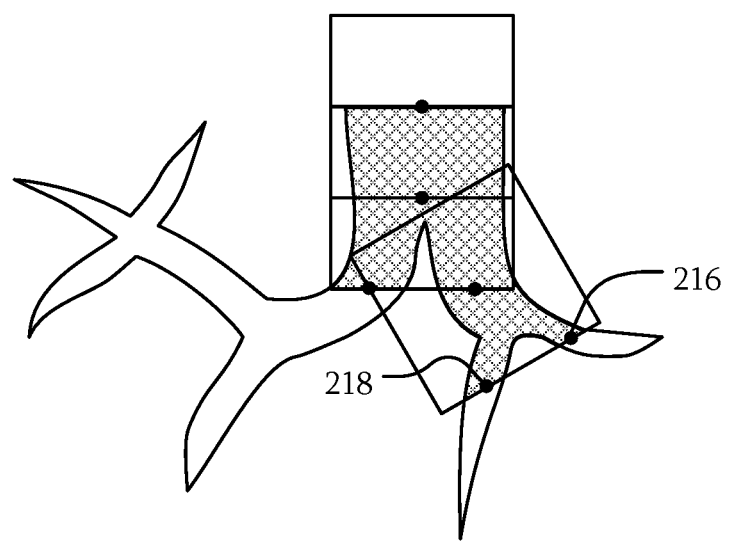
Figure 2I:
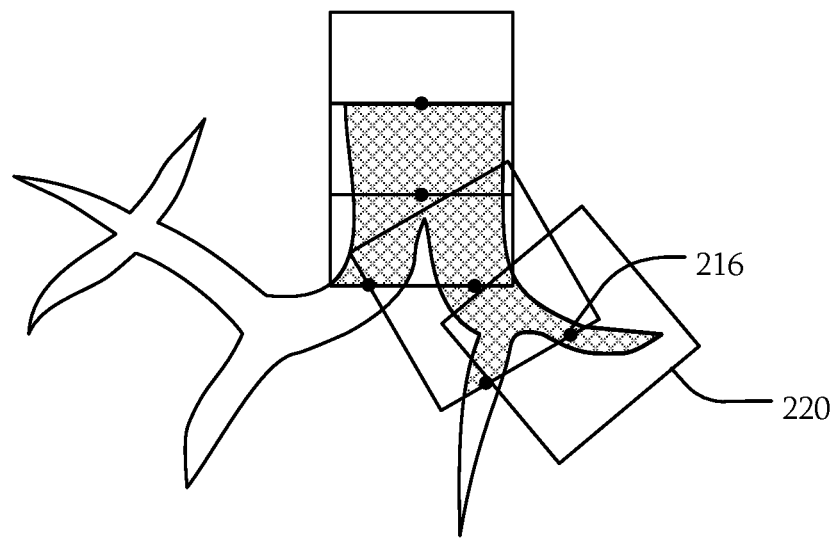
Figure 2J:
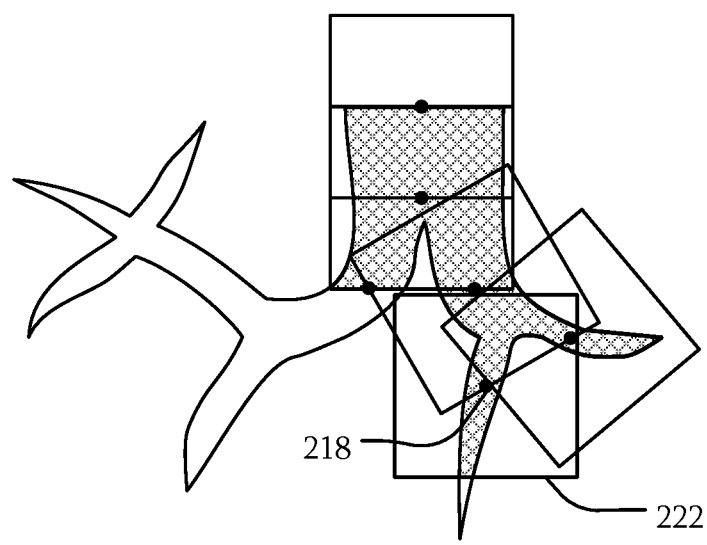
Figure 2K:
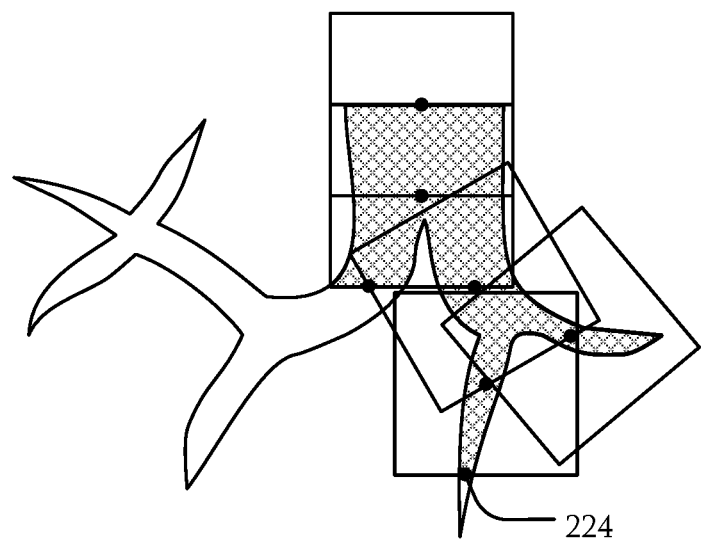
Figure 2L:
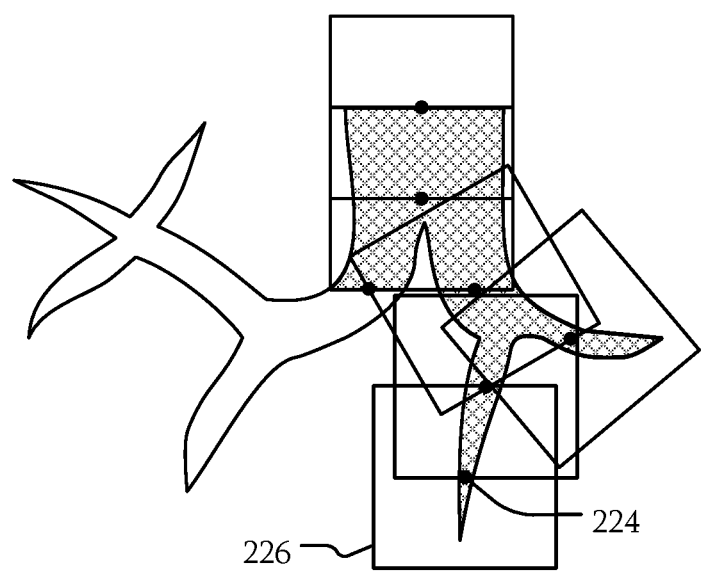
Figure 2M:
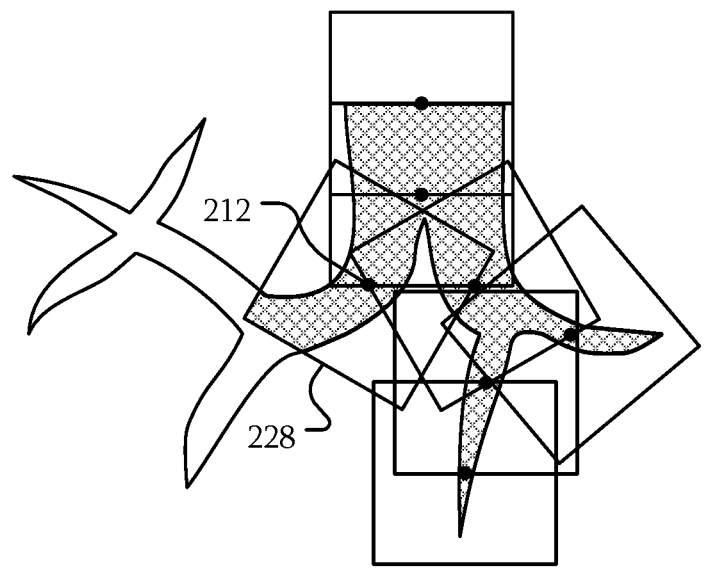
Figure 2N:
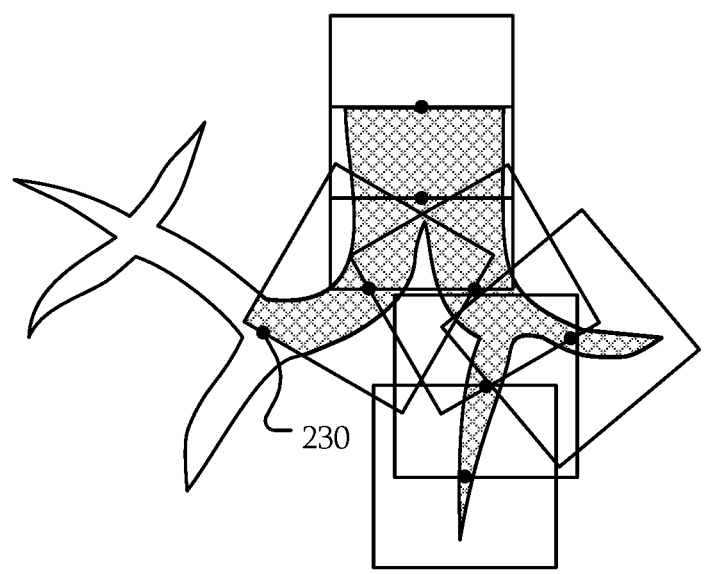
Figure 2O:
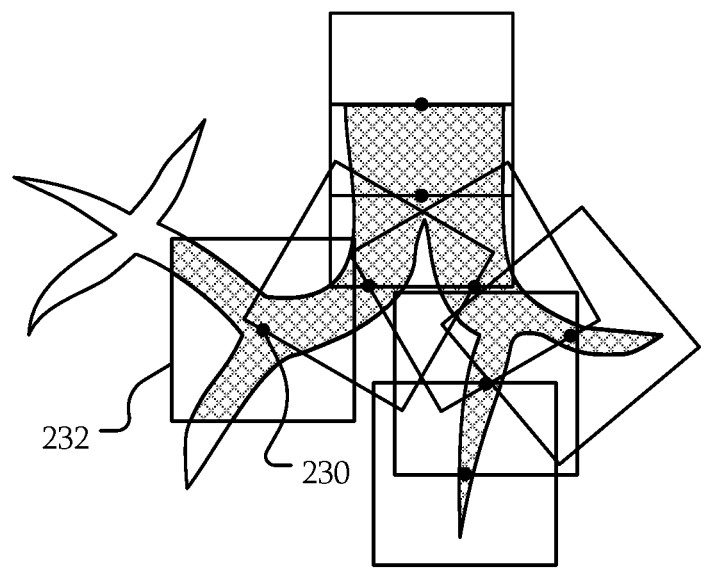
Figure 2P:
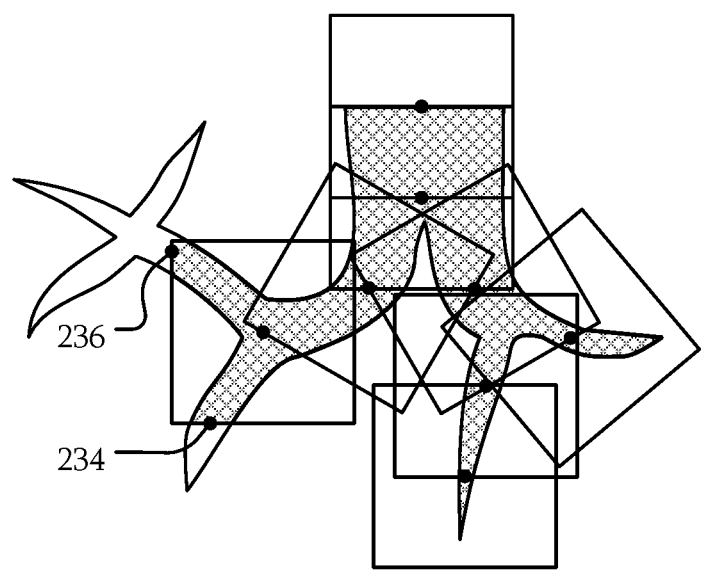
Figure 2Q:
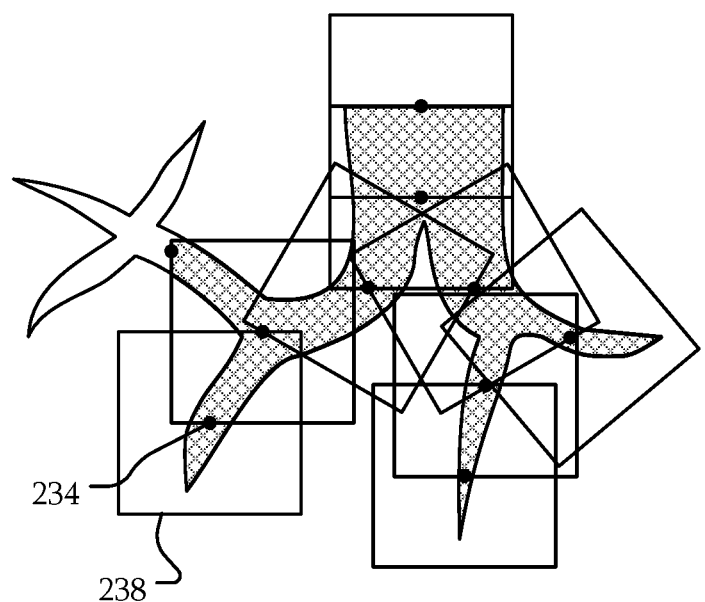
Figure 2R:
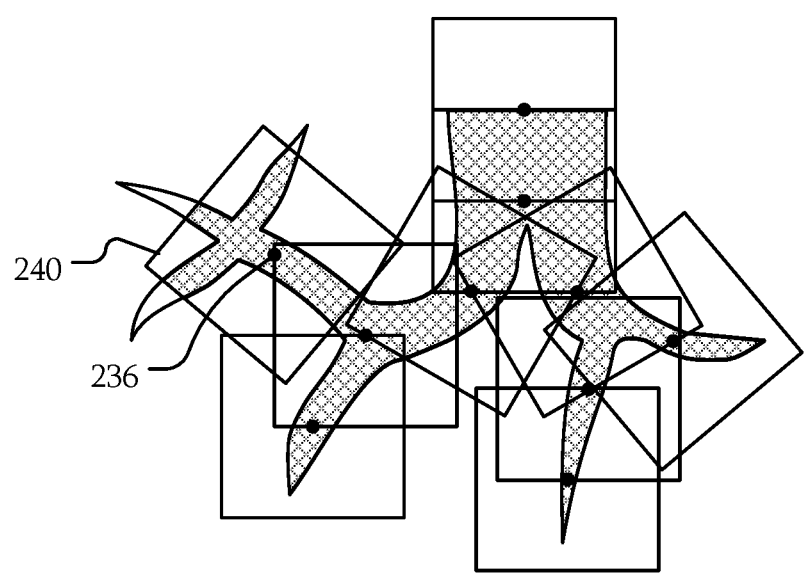
Figure 2S:
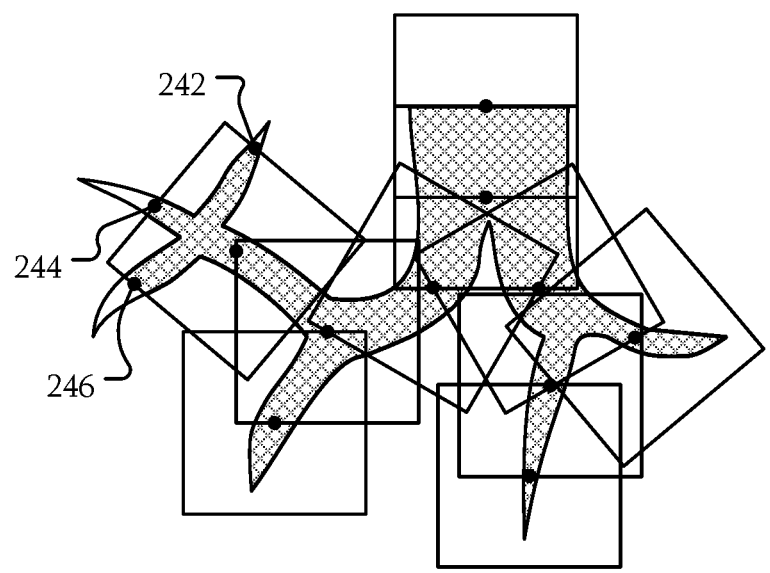
Figure 2T:
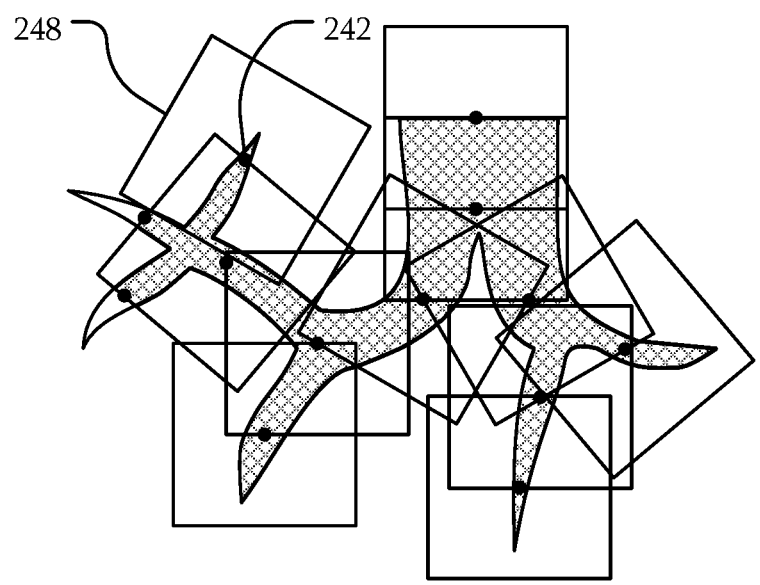
Figure 2U:
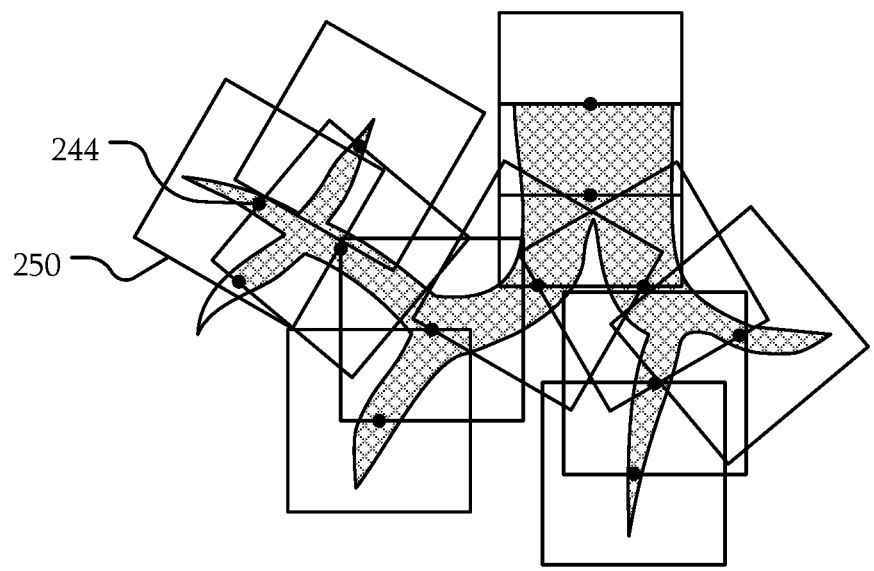
Figure 2V:
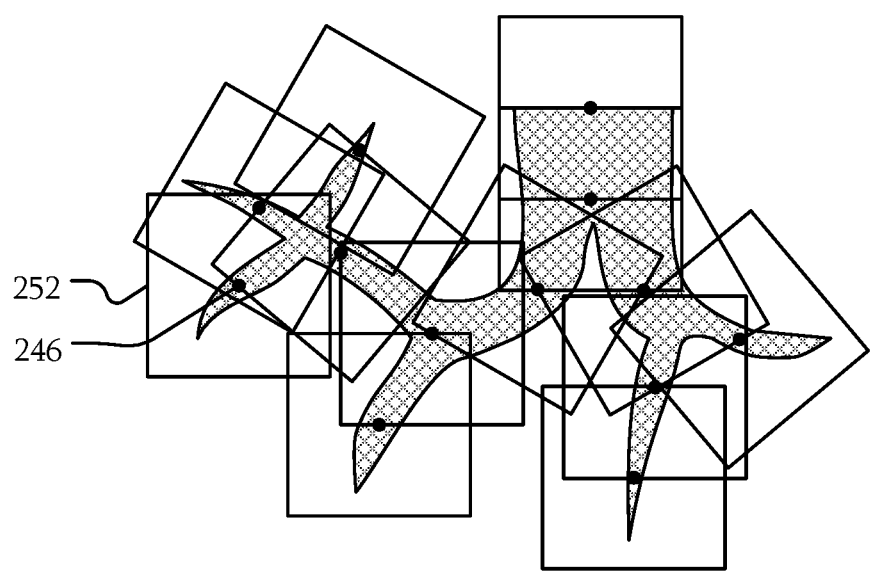

FIG. 2A-2V are diagrams of an example of segmenting a branching structure in an image according to some embodiments. Referring to FIG. 2A, branching structure 200 is an example of a branching structure in an image 102. A 2-dimensional branching structure is used as an example; however, the techniques may be similarly applied to n-dimensional images 102. Referring to FIG. 2B, a starting feature 202 is determined. Here a point is used as an example of a feature.

Referring to FIG. 2C, a subregion 204 of the image is selected and segmented. The result is the segmented branching structure indicated by the shading. Referring to FIG. 2D, a next feature 206 is found based on the segmented branching structure. Here, the next feature 206 is a point at an edge of the subregion 204 where the segmented branching structure reaches the edge.

Referring to FIG. 2E, a new subregion 208 is selected based on the feature 206. In an embodiment, the new subregion 208 may be orthogonal to an earlier subregion 204. The subregion 208 is segmented resulting in a new segmented branching structure. Here, for ease of illustration, the new segmented branching structure is illustrated as already combined with the previous segmented branching structure. In other embodiments, the new segmented branching structure may be stored separately and combined later.

Referring to FIG. 2F, from the new segmented branching structure, two features 210 and 212 are found. Referring to FIG. 2G, feature 210 is used to select subregion 214. In another embodiment, the subregion 214 may be non-orthogonal to an earlier subregion 208. The orientation of the subregion 214 may be determined by an earlier segmented branching structure. The subregion 214 is segmented resulting in a new segmented branching structure that is added to the combined segmented branching structure. Referring to FIG. 2H, similar to FIG. 2F, two features 216 and 218 are found.

Referring to FIG. 2I, feature 216 is used to select subregion 220. The subregion 220 is segmented resulting in a new segmented branching structure that is added to the combined segmented branching structure. However, no new features were found. In particular, the segmented branching structure found using subregion 220 was the end of that local branching structure.

Referring to FIG. 2J, feature 218 is used to select subregion 222. Feature 218 was a feature that remained after the path including feature 216 ended with no new features. The subregion 222 is segmented resulting in a new segmented branching structure that is added to the combined segmented branching structure. Referring to FIG. 2K, a new feature 224 is found.

Referring to FIG. 2L, feature 224 is used to select subregion 226. The subregion 226 is segmented resulting in a new segmented branching structure that is added to the combined segmented branching structure. Similar to FIG. 2I, no new features were found indicating the end of that local branching structure.

Referring to FIG. 2M, remaining feature 212 from FIG. 2F is used to select subregion 228. Feature 212 was a feature that remained after the path including feature 210 ended with no new features. The subregion 228 is segmented resulting in a new segmented branching structure that is added to the combined segmented branching structure. Referring to FIG. 2N, a new feature 230 is found.

Referring to FIG. 2O, a new subregion 232 is selected based on the feature 230. The subregion 232 is segmented resulting in a new segmented branching structure that is combined with the previous segmented branching structure.

Referring to FIG. 2P, two features 234 and 236 are found. Referring to FIG. 2Q feature 234 is used to select subregion 238. The subregion 238 is segmented resulting in a new segmented branching structure that is added to the combined segmented branching structure. Similar to FIGS. 2I and 2L, no new features were found indicating the end of that local branching structure.

Referring to FIG. 2R, remaining feature 236 from FIG. 2P is used to select subregion 240. Feature 236 was a feature that remained after the path including feature 234 ended with no new features. The subregion 240 is segmented resulting in a new segmented branching structure that is added to the combined segmented branching structure. Referring to FIG. 2S, new features 242, 244, and 246 are found.

Referring to FIGS. 2T, 2U, and 2V, for each of features 242, 244, and 246, the associated subregions 248, 250, and 252, respectively result in a new segmented branching structure. These segmented branching structures are each the end of the respective branches. As a result, all features including the starting feature and found features have resulted in subregions that were segmented to generate a combined segmented branching structure.

Figure 3:
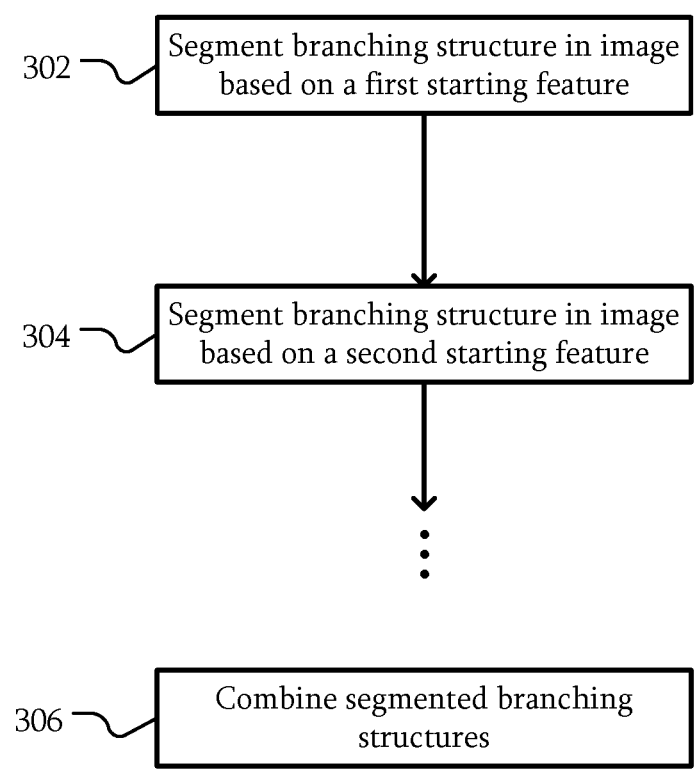
FIG. 3 is a block diagram of techniques of segmenting a branching structure according to some embodiments.

FIG. 3 is a block diagram of techniques of segmenting a branching structure according to some embodiments. In 302, a segmented branching structure is generated based on a first starting feature in an image. This operation may include operations described above with respect to FIGS. 1 and 2.

In 304, a segmented branching structure is generated based on a second starting feature in an image. This operation may again be similar to that described above with respect to FIGS. 1 and 2. However, the second starting feature may be different than the first. A user may be presented with the segmented branching structure from 302. The user may then select a new starting feature where improvement is desired. For example, a region of the segmented branching structure may need to be improved. A portion of the branching structure may have been missed by the processing, more detail or resolution is desired, or the like. The input may indicate where further segmentation should be performed. In another embodiment, a model representing a typical branching structure may be compared to the generated branching structure to determine potential missing portions of the branching structure. The potential missing portions may be used to determine a second or subsequent starting feature indicating where further segmentation should be performed.

The number of additional segmented branching structures generated may be 2 or more as indicated by the ellipsis. In 306, the segmented branching structures may be combined. For example, the segmented branching structures may be combined in an AND operation, an OR operation, a concatenation operation, a weighted combination or the like.

Figure 4:
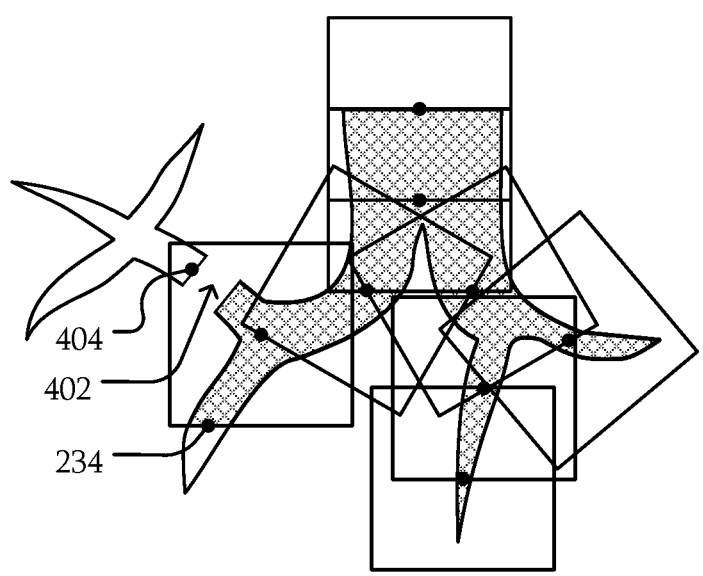
FIG. 4 is a diagram of an example of segmenting a branching structure having a discontinuity in an image according to some embodiments.

FIG. 4 is a diagram of an example of segmenting a branching structure having a discontinuity in an image according to some embodiments. FIG. 4 is similar to the state represented by FIG. 2P. However, a discontinuity 402 is present in the branching structure. For example, the discontinuity may be a tumor in the path of a vascular system of a liver, an artifact of the image, or the like. As a result, the feature 236 of FIG. 2P may not be found. The segmented branching structure may not include the portions found in FIGS. 2R-2V.

However, another feature 404 may be used as a starting feature. The remainder of the branching structure may be segmented similar to the segmentation in FIGS. 2R-2V. The result is two segmented branching structures that may be combined together as described with respect to FIG. 3. As a result, a combined segmented branching structure may be generated where the discontinuity may have otherwise only resulted in one of the two segmented branching structures. Although a single discontinuity 402 has been used as an example, in other embodiments segmented branching structures may be generated when there are multiple discontinuities 402.

In some embodiments, attributes of the subregion may change from iteration to iteration in FIG. 1. For example, in FIGS. 2C-2V, the subregion was a square having a rotation that may be different across iterations. In some embodiments, the subregion may have changed shape across iterations. For example, the subregion selected based on a feature may have a size and/or orientation based on the segmented branching structure leading to that feature. In some embodiments, the subregion may not be rotated relative to another subregion. For example, one or more of the subregions may be aligned to each other, the image 102, a major structure segmented in the segmented branching structure, or the like.

Figure 5:
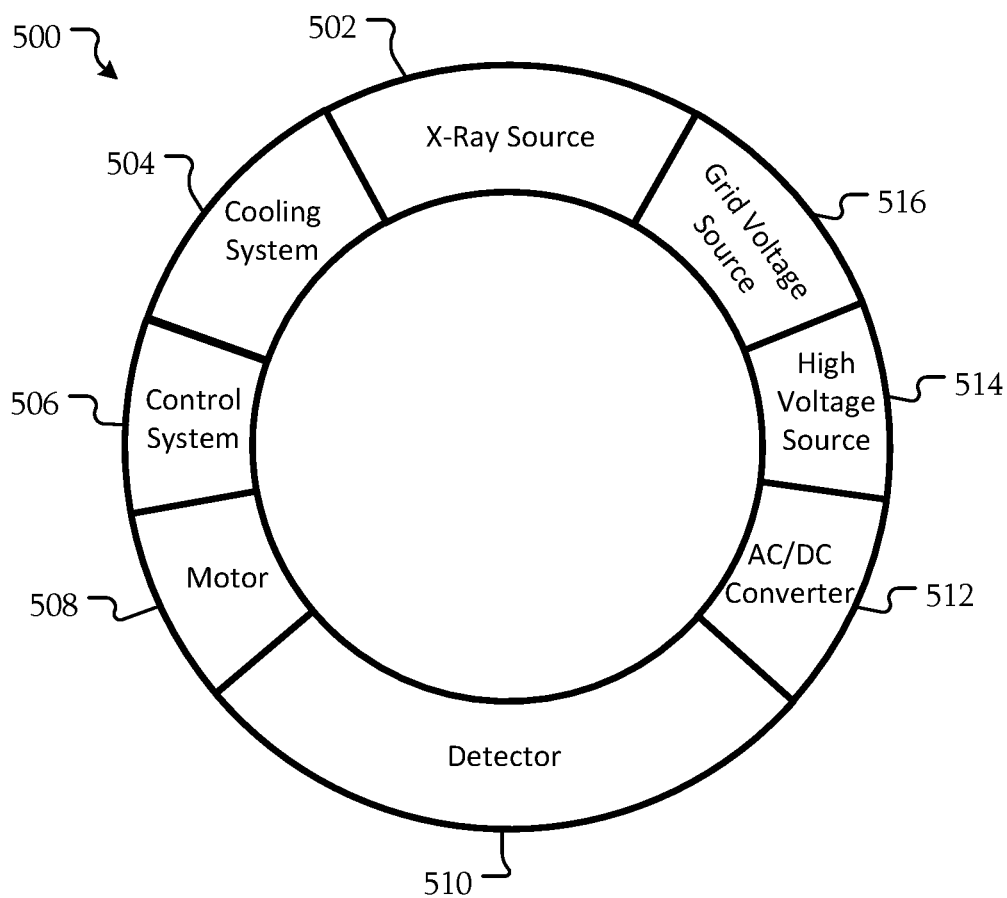
FIG. 5 is a block diagram of a computerized tomography (CT) gantry according to some embodiments.

FIG. 5 is a block diagram of a computerized tomography (CT) system according to some embodiments. In some embodiments, the CT system 500 includes an x-ray source 502, a cooling system 504, a control system 506, a motor drive 508, a detector 510, an AC/DC converter 512, a high voltage source 514, and a grid voltage source 516. The control system 506 may be configured to perform the segmentation on an image generated by the detector 510. For example, the control system 506 may include a central processing unit (CPU), memory, a graphics processing unit (GPU), other peripheral devices, or the like to perform the operations described above. Although particular components have been used as examples of components that may be mounted on a CT gantry, in other embodiments, the other components may be different.

Figure 6:
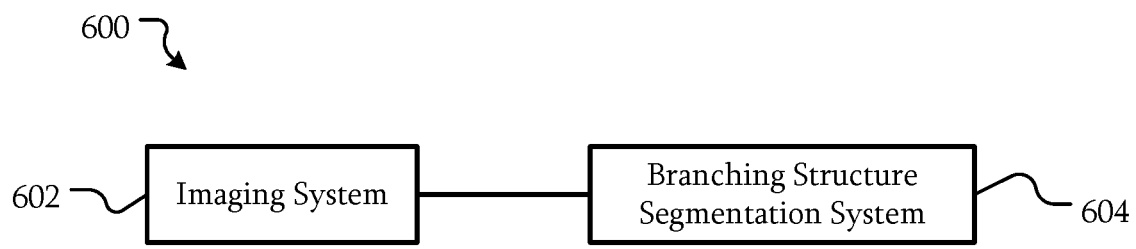
FIG. 6 is a block diagram of a system according to some embodiments.

FIG. 6 is a block diagram of a system according to some embodiments. The system 600 includes an imaging system 602 and a branching structure segmentation system 604. The imaging system 602 may include imaging devices configured to generate an image that may represent a branching structure as described above. For example, the imaging system 602 may include a camera, an x-ray system such as the CT system described above or the like, an ultrasonic imager, or other imaging devices that are capable of generating an image of a branching structure.

The branching structure segmentation system 604 may be configured to receive an image including a branching structure from the imaging system 602. The branching structure segmentation system 604 may include a CPU, a memory, a GPU, other peripheral devices, or the like to perform the operations described above.

Figure 7:
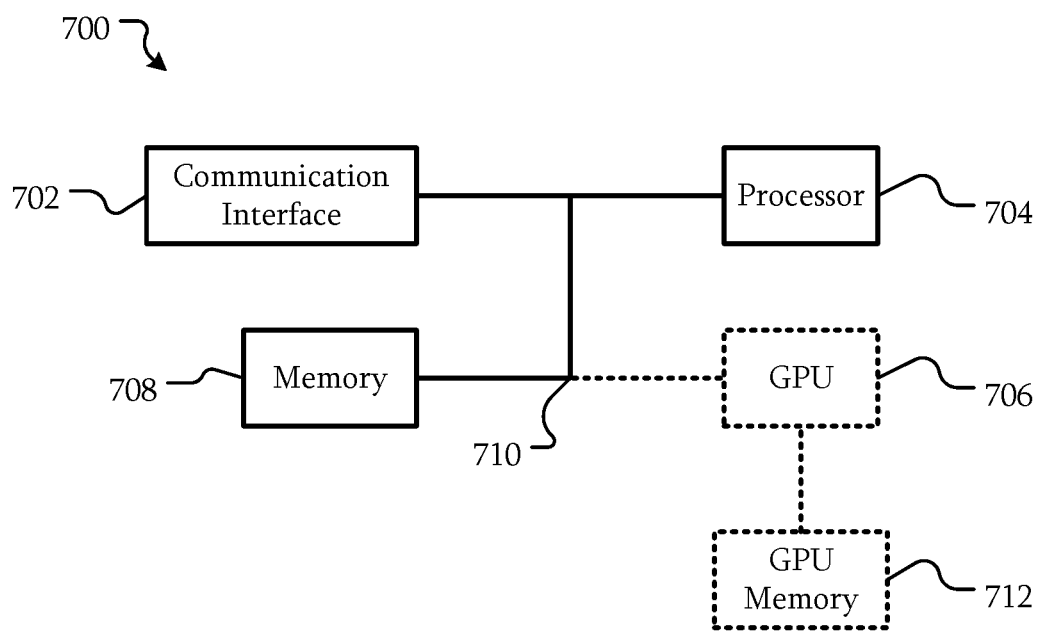
FIG. 7 is a block diagram of a branching structure segmentation system according to some embodiments.

FIG. 7 is a block diagram of a branching structure segmentation system according to some embodiments. The branching structure segmentation system 700 includes a communication interface 702, a processor 704, and a memory 708. The communication interface 702, processor 704, GPU 706, and memory 708 may be coupled by a bus 710.

The communication interface 702 may be configured to facilitate communication between external systems and the CPU 704 and/or other components. In particular, the communication interface 702 may be configured to receive an image representing a branching structure from an imaging system. In some embodiments, the communication interface 702 may include a as universal serial bus (USB), small computer system interface (SCSI), peripheral component interconnect express (PCIe), nonvolatile memory express (NVMe), mobile PCIe (M-PCIe), advanced technology attachment (ATA), parallel ATA (PATA), serial ATA (SATA), serial attached SCSI (SAS), integrated drive electronics (IDE), universal flash storage (UFS), Firewire, and/or the like. In other embodiments, the communication interface 702 may include an interface to a communication network such as an Ethernet, a Fibre Channel network, or the like.

The processor 704 may include a variety of circuits. For example, the processor may include a general-purpose processor, a digital signal processor (DSP), an application specific integrated circuit, a microcontroller, a programmable logic device, discrete circuits, a combination of such devices, or the like. The processor 704 may include internal portions, such as registers, cache memory, processing cores, or the like, and may also include external interfaces, such as address and data bus interfaces, interrupt interfaces, or the like. Although only one processor 704 is illustrated in system 700, multiple processors 704 may be present. In addition, other interface devices, such as logic chipsets, hubs, memory controllers, communication interfaces, or the like may be part of the system 700 to connect the processor 704 to internal and external components.

The memory 708 may include a variety of circuits. Examples of the memory 708 include a dynamic random access memory (DRAM), a double data rate synchronous dynamic random access memory (DDR SDRAM) according to various standards such as DDR, DDR2, DDR3, DDR4, static random access memory (SRAM), non-volatile memory such as flash memory, spin-transfer torque magentoresistive random access memory (STT-MRAM), Phase-Change RAM, nanofloating gate memory (NFGM), or polymer random access memory (PoRAM), magnetic or optical media, or the like. The memory 708 may be configured to store instructions that, when executed, cause the processor 704 or other components such as a GPU 706 to perform operations described herein.

In some embodiments, the system 700 includes a GPU 706. The GPU 706 may be configured to access the memory 708 and/or may be configured to access a dedicated memory 712 during operation. The GPU 706 may be configured to implement specific portions of the operations described herein such as the determination of a starting feature, the segmentation of a subregion and/or the finding of the next features. In some embodiments, the processor 704 may not be part of the system 700 and the GPU 706 may form the processor for the system 700.

Embodiments described herein improve on other techniques of segmenting branching structures in an image. In some embodiments, an advantage of using techniques described herein improves a computer's performance in segmenting a branching structure represented in the image 102. In particular, a subregion of the image 102 is selected before it is processed by computational and/or memory intensive operations. For example, a neural network need not process the entire image 102 as only subregions based on the starting feature and subsequently found features based off of the starting feature are processed. Such a neural network will have a smaller processing and/or memory requirement than one that would process the entire image 102. The smaller footprint may allow for a more computational or resource intensive neural network to be used as that neural network processes the smaller subregion of the image 102. Moreover, the use of techniques based on machine learning such as a neural network may also improve the performance and/or accuracy over other segmenting techniques such as watershed segmenting, flood filling, region growing, or the like that rely on fixed algorithms.

In addition, in some embodiments, less than all of the image 102 may be processed. For example, the sequence of subregions that are processed when following the branching structure in the image 102, may be smaller than the entire image 102. Other techniques such as watershed segmenting, flood filling, region growing, or the like may process the entire image 102.

Furthermore, in some embodiments, finding the next features using the segmented branching structure of a subregion may improve performance. In particular, the next features allow the segmenting to follow the branching structure, even if that branching structure extends beyond the size of the current subregion. The technique is not limited to following an expected sequence such as a sequence of vertebrae extending in one direction. Moreover, the use of an earlier segmented branching structure of a subregion may improve the segmenting in a related subregion.

Moreover, in some embodiments, the separation of the segmenting of a subregion and the finding of the next features may allow for independent and/or operational specific improvements that may otherwise be absent or more difficult with a unified segmenting technique. For example, a neural network that performs the segmenting of a subregion may be optimized in ways that could improve the segmenting but lead to decreased performance in finding the next features. The separate operation of finding next features allows for that operation to be independently optimized.

Some embodiments include a method, comprising: receiving an image 102 representing a branching structure; determining a starting feature of the branching structure;

selecting a subregion of the image 102 based on the starting feature; segmenting the branching structure in the subregion; generating a set of next features based on the segmented branching structure; and for each of the next features, repeating the selecting of the subregion based on the next feature, the segmenting of the branching structure, and the generating of the set of next features.

In some embodiments, the method further comprises repeating the selecting of the subregion, the segmenting of the branching structure, and the generating of the set of next features until each next feature has been used to select a subregion, segment the branching structure in the subregion, and generate a set of next features based on the segmented branching structure.

In some embodiments, the method further comprises combining the segmented branching structure based on the starting feature and segmented branching structures based on each of the next features.

In some embodiments, the method further comprises combining the combined segmented branching structure with a prior combined segmented branching structure.

In some embodiments, the branching structure is a liver vasculature.

In some embodiments, the method further comprises analyzing the image 102 representing the branching structure to determine the starting feature of the branching structure.

In some embodiments, the method further comprises receiving a manual designation of the starting feature of the branching structure.

In some embodiments, segmenting the branching structure in the subregion comprises segmenting the branching structure in the subregion based on a previously segmented branching structure in a previous subregion.

In some embodiments, the subregion overlaps the previous subregion.

In some embodiments, segmenting the branching structure in the subregion comprises generating the segmented branching structure using a first convolutional neural network.

In some embodiments, the first convolutional neural network is a U-net architecture.

In some embodiments, generating the set of next features comprises generating the set of next features using a second convolutional neural network.

In some embodiments, each subregion has a dimension of at least two image elements.

In some embodiments, generating the set of next features comprises generating multiple features for the set of next features.

A system, comprising: a communication interface configured to receive an image 102 representing a branching structure; and a processor 704, 706 configured to: determine a starting feature of the branching structure; select a subregion of the image 102 based on the starting feature; segment the branching structure in the subregion; generate a set of next features based on the segmented branching structure; and for each of the next features, repeat the selecting of the subregion based on the next feature, the segmenting of the branching structure, and the generating of the set of next features.

In some embodiments, the processor 704, 706 is further configured to: repeat the selecting of the subregion, the segmenting of the branching structure, and the generating of the set of next features until each next feature has been used to select a subregion, segment the branching structure in the subregion, and generate a set of next features based on the segmented branching structure In some embodiments, the processor 704, 706 is further configured to: combine the segmented branching structure based on the starting feature and segmented branching structures based on each of the next features; and combine the combined segmented branching structure with a prior combined segmented branching structure.

In some embodiments, the image 102 includes a discontinuity dividing the branching structure into a first branching structure and a second branching structure; the prior combined segmented branching structure was segmented from the first branching structure; and the starting feature is a feature of the second branching structure.

In some embodiments, the branching structure is a vasculature or bronchial tree. In some embodiments, the branching structure is a vasculature of a living entity such as a vasculature of a liver, kidney, heart or other organ of a human or an animal or a vasculature of a plant.

In some embodiments, the processor 704, 706 is further configured to: segment the branching structure in the subregion by segmenting the branching structure in the subregion based on a previously segmented branching structure in a previous subregion.

In some embodiments, the processor 704, 706 is further configured to: analyze the image 102 representing the branching structure to determine the starting feature of the branching structure.

Some embodiments include a system, comprising: means for receiving an image representing a branching structure; means for determining a starting feature of the branching structure; means for selecting a subregion of the image based on the starting feature; means for segmenting the branching structure in the subregion; means for generating a set of next features based on the segmented branching structure; and means for, for each of the next features, repeating the selecting of the subregion based on the next feature, the segmenting of the branching structure, and the generating of the set of next features. Examples of the means for receiving an image include the communication interface 702, the bus 710, the processor 704, the GPU 706, the memory 708, and the GPU memory 712. Examples of the means for determining a starting feature include the bus 710, the processor 704, the GPU 706, the memory 708, and the GPU memory 712. Examples of the means for selecting a subregion include the bus 710, the processor 704, the GPU 706, the memory 708, and the GPU memory 712. Examples of the means for generating a set of next features include the bus 710, the processor 704, the GPU 706, the memory 708, and the GPU memory 712. Examples of the means for segmenting the branching structure include the bus 710, the processor 704, the GPU 706, the memory 708, and the GPU memory 712. Examples of the means for, for each of the next features, repeating the selecting of the subregion include the bus 710, the processor 704, the GPU 706, the memory 708, and the GPU memory 712. These examples of the above means may be configured to perform the operations described above.

In some embodiments, the system further comprises means for segmenting the branching structure in the subregion comprises segmenting the branching structure in the subregion based on a previously segmented branching structure in a previous subregion. Examples of the means for segmenting the branching structure in the subregion based on a previously segmented branching structure include the bus 710, the processor 704, the GPU 706, the memory 708, and the GPU memory 712. These examples of the above means may be configured to perform the operations described above.

Although the structures, devices, methods, and systems have been described in accordance with particular embodiments, one of ordinary skill in the art will readily recognize that many variations to the particular embodiments are possible, and any variations should therefore be considered to be within the spirit and scope disclosed herein. Accordingly, many modifications may be made by one of ordinary skill in the art without departing from the spirit and scope of the appended claims.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the claims beginning with claim [x] and ending with the claim that immediately precedes this one," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 6 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed to cover the corresponding structure, material, or acts described herein and equivalents thereof in accordance with 35 U.S.C. § 112(f). Embodiments of the invention in which an exclusive property or privilege is claimed are defined as follows.

The invention claimed is:

1. A method, comprising:
   receiving an image representing a branching structure;
   determining a starting feature of the branching structure;
   selecting a subregion of the image based on the starting feature;
   segmenting the branching structure in the subregion to generate a fully segmented branching structure output for the subregion;
   generating a set of next features based on the fully segmented branching structure output, wherein:
      the set of next features indicates where the branching structure in the image continues beyond the subregion; and
      generating the set of next features comprises analyzing the fully segmented branching structure output with a neural network to generate the set of next features; and
   for each of the next features, repeating the selecting of the subregion based on the next feature, the segmenting of the branching structure, and the generating of the set of next features.

2. The method of claim 1, further comprising:
   repeating the selecting of the subregion, the segmenting of the branching structure, and the generating of the set of next features until each next feature has been used to select a subregion, segment the branching structure in the subregion, and generate a set of next features based on the fully segmented branching structure output.

3. The method of claim 2, further comprising:
   combining the segmented branching structure based on the starting feature and segmented branching structures based on each of the next features.

4. The method of claim 3, further comprising:
   combining the combined segmented branching structure with a prior combined segmented branching structure.

5. The method of claim 4, wherein:
   the image includes a discontinuity dividing the branching structure into a first branching structure and a second branching structure;
   the prior combined segmented branching structure was segmented from the first branching structure; and
   the starting feature is a feature of the second branching structure.

6. The method of claim 1, wherein:
   segmenting the branching structure in the subregion comprises segmenting the branching structure in the subregion based on a previously segmented branching structure in a previous subregion.

7. The method of claim 6, wherein:
   the subregion overlaps the previous subregion.

8. The method of claim 1, wherein:
   segmenting the branching structure in the subregion comprises generating the segmented branching structure using a first convolutional neural network.

9. The method of claim 8, wherein:
   the first convolutional neural network is a U-net architecture.

10. The method of claim 8, wherein:
    generating the set of next features comprises generating the set of next features using a second convolutional neural network.

11. The method of claim 1, further comprising:
    analyzing the image representing the branching structure to determine the starting feature of the branching structure.

12. The method of claim 1, wherein generating the set of next features comprises generating multiple features for the set of next features.

13. The method of claim 1, wherein the branching structure is a vasculature of a living entity.

14. The method of claim 1, wherein each subregion has a dimension of at least two image elements.

15. The method of claim 1, wherein:
    generating the set of next features further comprises generating each next feature of the set of next features on a perimeter of the subregion.

16. A system, comprising:
    a communication interface configured to receive an image representing a branching structure; and
    a processor configured to:
       determine a starting feature of the branching structure;
       select a subregion of the image based on the starting feature;
       segment the branching structure in the subregion to generate a fully segmented branching structure output for the subregion;
       generate a set of next features based on the fully segmented branching structure output, wherein:

the set of next features indicates where the branching structure in the image continues beyond the subregion; and the processor is further configured to generate the set of next features by analyzing the fully segmented branching structure output with a neural network to generate the set of next features; and for each of the next features, repeat the selecting of the subregion based on the next feature, the segmenting of the branching structure, and the generating of the set of next features.

17. The system of claim 16, wherein the processor is further configured to:

repeat the selecting of the subregion, the segmenting of the branching structure, and the generating of the set of next features until each next feature has been used to select a subregion, segment the branching structure in the subregion, and generate a set of next features based on the fully segmented branching structure output.

18. The system of claim 16, wherein the processor is further configured to:

combine the segmented branching structure based on the starting feature and segmented branching structures based on each of the next features; and combine the combined segmented branching structure with a prior combined segmented branching structure.

19. The system of claim 16, wherein the processor is further configured to:

segment the branching structure in the subregion by segmenting the branching structure in the subregion based on a previously segmented branching structure in a previous subregion.

20. A system, comprising:

means for receiving an image representing a branching structure;

means for determining a starting feature of the branching structure;

means for selecting a subregion of the image based on the starting feature;

means for segmenting the branching structure in the subregion to generate a fully segmented branching structure output for the subregion;

means for generating a set of next features based on the fully segmented branching structure output, wherein:

the set of next features indicates where the branching structure in the image continues beyond the subregion; and the means for generating the set of next features comprises means for analyzing the fully segmented branching structure output with a neural network to generate the set of next features; and means for, for each of the next features, repeating the selecting of the subregion based on the next feature, the segmenting of the branching structure, and the generating of the set of next features.

21. The system of claim 20, further comprising:

means for segmenting the branching structure in the subregion comprises segmenting the branching structure in the subregion based on a previously segmented branching structure in a previous subregion.

\* \* \* \* \*